(12) United States Patent
Sternik (10) Patent No.: US 11,266,389 B2
(45) Date of Patent: Mar. 8, 2022

(54) BODY PART REPOSITIONING APPARATUS AND METHOD

(71) Applicant: Tel HaShomer Medical Research Infrastructure and Services Ltd., Ramat-Gan (IL)

(72) Inventor: Leonid Sternik, Kiryat-Ono (IL)

(73) Assignee: Tel HaShomer Medical Research infrastructure and Services Ltd., Ramat-Gan (IL)

( * ) Notice: Subject to any disclaimer, the term of this patent is extended or adjusted under 35 U.S.C. 154(b) by 0 days.

(21) Appl. No.: 16/408,506

(22) Filed: May 10, 2019

(65) Prior Publication Data
US 2019/0321020 A1    Oct. 24, 2019

Related U.S. Application Data

(63) Continuation of application No. 14/232,573, filed as application No. PCT/IL2012/000278 on Jul. 9, 2012, now Pat. No. 10,292,689.
(Continued)

(30) Foreign Application Priority Data

Mar. 19, 2012 (IL) .......................................... 218737

(51) Int. Cl.
*A61B 17/00*  (2006.01)
*A61B 17/12*  (2006.01)
(Continued)

(52) U.S. Cl.
CPC ...... *A61B 17/00234* (2013.01); *A61B 17/064* (2013.01); *A61B 17/083* (2013.01);
(Continued)

(58) Field of Classification Search
CPC ............ A61B 17/00234; A61B 17/064; A61B 17/083; A61B 17/12013; A61B 17/12122;
(Continued)

(56) References Cited

U.S. PATENT DOCUMENTS 2,235,350 A    3/1941  Anderson
5,224,497 A *  7/1993  Ehlers ................ A61B 17/0057
                                                    128/898
(Continued)

FOREIGN PATENT DOCUMENTS

EP          1579823        9/2005
WO    WO 2008/020975       2/2008
(Continued)

OTHER PUBLICATIONS

Applicant-Initiated Interview Summary dated Nov. 3, 2017 From the US Patent and Trademark Office Re. U.S. Appl. No. 14/232,573. (3 pages).
(Continued)

*Primary Examiner* — Erich G Herbermann (57) ABSTRACT

A device for manipulating the left atrial appendage (LAA) of a heart, including:
  an elongated and hollow guide instrument which is shaped and sized to be transvascularly and transseptally introducible into the left atrium (LA);
a suction channel passing through the guide instrument, the suction channel terminating with a concave holder, wherein the suction channel and the concave holder are shaped and sized to be enclosed within a lumen of the guide instrument during the transvascular and transseptal introduction into the LA and to forwardly extend from the lumen of the guide instrument after reaching the LA, and wherein the concave holder is configured to radially expand;
(Continued)

a loop fastener shaped and sized to be enclosed within the lumen of the guide instrument during the transvascular and transseptal introduction into the LA and to forwardly extend from the lumen of said guide instrument.

11 Claims, 10 Drawing Sheets

Related U.S. Application Data (60) Provisional application No. 61/457,928, filed on Jul. 11, 2011.

(51) Int. Cl.
| | |
|---|---|
| A61B 17/30 | (2006.01) |
| A61B 17/064 | (2006.01) |
| A61B 17/08 | (2006.01) |
| A61B 17/221 | (2006.01) |

(52) U.S. Cl.
CPC .. *A61B 17/12013* (2013.01); *A61B 17/12122* (2013.01); *A61B 17/12131* (2013.01); *A61B 17/221* (2013.01); *A61B 17/30* (2013.01); *A61B 17/00491* (2013.01); *A61B 2017/00243* (2013.01); *A61B 2017/308* (2013.01); *A61B 2217/005* (2013.01)

(58) Field of Classification Search
CPC . A61B 17/12131; A61B 17/221; A61B 17/30; A61B 17/00491; A61B 2017/00243; A61B 2017/308; A61B 2217/17005; A61B 17/12022; A61B 17/12031
See application file for complete search history.

(56) References Cited

U.S. PATENT DOCUMENTS

| | | | | |
|---|---|---|---|---|
| 5,423,830 | A | * | 6/1995 | Schneebaum .......... A61B 18/10 606/110 |
| 5,792,153 | A | | 8/1998 | Swain et al. |
| 6,152,936 | A | * | 11/2000 | Christy .............. A61B 17/0483 606/139 |
| 6,383,198 | B1 | * | 5/2002 | Hamilton ......... A61B 17/22031 606/110 |
| 7,427,279 | B2 | | 9/2008 | Frazier et al. |
| 8,647,367 | B2 | | 2/2014 | Kassab et al. |
| 8,784,469 | B2 | | 7/2014 | Kassab |
| 2001/0041914 | A1 | | 11/2001 | Frazier et al. |
| 2003/0158563 | A1 | | 8/2003 | McClellan et al. |
| 2004/0044364 | A1 | * | 3/2004 | DeVries ............... A61B 17/064 606/213 |
| 2005/0021016 | A1 | | 1/2005 | Malecki et al. |
| 2007/0043344 | A1 | | 2/2007 | McAuley |
| 2007/0083082 | A1 | | 4/2007 | Kiser et al. |
| 2007/0225734 | A1 | | 9/2007 | Bell et al. |
| 2008/0033241 | A1 | * | 2/2008 | Peh ...................... A61B 1/3137 600/109 |
| 2008/0255427 | A1 | * | 10/2008 | Satake ................. A61B 17/083 600/204 |
| 2008/0294175 | A1 | | 11/2008 | Bardsley et al. |
| 2008/0312664 | A1 | | 12/2008 | Bardsley et al. |
| 2009/0326518 | A1 | * | 12/2009 | Rabin .................... A61B 17/30 606/1 |
| 2010/0145361 | A1 | | 6/2010 | Francischelli et al. |
| 2010/0191279 | A1 | | 7/2010 | Kassab et al. |
| 2010/0312256 | A1 | | 12/2010 | Kassab et al. |
| 2011/0077672 | A1 | | 3/2011 | Fleischman et al. |
| 2011/0082495 | A1 | | 4/2011 | Ruiz |
| 2012/0035622 | A1 | | 2/2012 | Kiser et al. |
| 2014/0018831 | A1 | | 1/2014 | Kassab et al. |
| 2014/0171733 | A1 | | 6/2014 | Sternik |
| 2016/0106437 | A1 | | 4/2016 | van der Burg et al. |
| 2017/0065283 | A9 | | 3/2017 | Kassab et al. |
| 2019/0262003 | A1 | | 8/2019 | Kiser et al. |
| 2020/0100796 | A1 | | 4/2020 | Berger et al. |

FOREIGN PATENT DOCUMENTS

| | | |
|---|---|---|
| WO | WO 2012/103556 | 8/2012 |
| WO | WO 2013/008231 | 1/2013 |
| WO | WO 2018/178979 | 10/2018 |

OTHER PUBLICATIONS

Communication Pursuant to Article 94(3) EPC dated Apr. 19, 2017 From the European Patent Office Re. Application No. 12811116.8. (9 Pages).
Communication Pursuant to Article 94(3) EPC dated Oct. 31, 2018 From the European Patent Office Re. Application No. 12811116.8. (7 Pages).
Communication Pursuant to Rules 161(2) and 162 EPC dated Feb. 27, 2014 From the European Patent Office Re. Application No. 12811116.8. (3 Pages).
International Preliminary Report on Patentability dated Jan. 14, 2014 From the International Bureau of WIPO Re. Application No. PCT/IL2012/000278. (10 Pages).
International Search Report and the Written Opinion dated Aug. 14, 2018 From the International Searching Authority Re. Application No. PCT/IL2018/050353. (22 Pages).
International Search Report dated Nov. 11, 2012 From the International Searching Authority Re. Application No. PCT/IL2012/000278. (4 Pages).
Invitation to Pay Additional Fees, Communication Relating to the Results of the Partial International Search and the Provisional Opinion dated Jun. 20, 2018 From the International Searching Authority Re. Application No. PCT/IL2018/050353. (16 Pages).
Notice Of Allowance dated Jan. 9, 2019 From the US Patent and Trademark Office Re. U.S. Appl. No. 14/232,573. (13 pages).
Official Action dated Sep. 8, 2016 From the US Patent and Trademark Office Re. U.S. Appl. No. 14/232,573. (12 pages).
Official Action dated Sep. 14, 2017 From the US Patent and Trademark Office Re. U.S. Appl. No. 14/232,573. (18 pages).
Official Action dated Apr. 17, 2017 From the US Patent and Trademark Office Re. U.S. Appl. No. 14/232,573. (18 pages).
Official Action dated May 17, 2016 From the US Patent and Trademark Office Re. U.S. Appl. No. 14/232,573. (11 pages).
Official Action dated Sep. 20, 2018 From the US Patent and Trademark Office Re. U.S. Appl. No. 14/232,573. (24 pages).
Official Action dated Mar. 28, 2018 From the US Patent and Trademark Office Re. U.S. Appl. No. 14/232,573. (19 pages).
Official Action dated Sep. 28, 2015 From the US Patent and Trademark Office Re. U.S. Appl. No. 14/232,573. (11 pages).
Supplementary European Search Report and the European Search Opinion dated Feb. 27, 2015 From the European Patent Office Re. Application No. 12811116.8. (8 Pages).
Written Opinion dated Nov. 11, 2012 From the International Searching Authority Re. Application No. PCT/IL2012/000278. (9 Pages).
Written Opinion dated Oct. 23, 2012 From the International Searching Authority Re. Application No. PCT/IL2012/000278. (8 Pages).
Boston Scientific "Reducing the Risk of Stroke in Atrial Fibrillation With the Watchman™ Left Atrial Appendage (LAA) Closure Device", Boston Scientific, SH-282105-AA, Poster Leaflet, 2 P., Nov. 2014.
Hu et al. "Device-Based Approach to Prevention of Stroke in Atrial Fibrillation", The Journal of Innovations in Cardiac Rhythm Management, 6: 2038-2050, Jun. 2015.
Kreidieh et al. "Left Atrial Appendage Remodeling After Lariat Left Atrial Appendage Ligation", Circulation Arrhythm Electrophysiology, 8(6): 1351-1358, Published Online Oct. 20, 2015.
Omran "Left Atrial Appendage Anatomy: The LAA Is Unique as a Fingerprint, How to Close Those Successfully?", Euro PCR 2016, Slide Show, 37 P., 2016.
Piccini et al. "Left Atrial Appendage Occlusion: Rationale, Evidence, Devices, and Patient Selection", European Heart Journal, EHW330: 1-9, Advance Access Pubheation Sep. 13, 2016.

(56) References Cited

OTHER PUBLICATIONS

International Preliminary Report on Patentability dated Oct. 10, 2019 From the International Bureau of WIPO Re. Application No. PCT/IL2018/050353. (14 Pages).
Official Action dated Mar. 8, 2021 From the US Patent and Trademark Office Re. U.S. Appl. No. 16/497,821. (30 Pages).
Final Official Action dated Oct. 15, 2021 fromUS Patent and Trademark Office Re. U.S. Appl. No. 16/497,821. (20 pages).

* cited by examiner

SECTION A-A
SCALE 8:1

FIG. 7b

BODY PART REPOSITIONING APPARATUS AND METHOD

RELATED APPLICATIONS

This application is a continuation of U.S. patent application Ser. No. 14/232,573 filed on Jan. 13, 2014, which is National Phase of PCT Patent Application No. PCT/IL2012/000278 having International Filing Date of Jul. 9, 2012, which claims the benefit of priority of Israel Patent Application No. 218737 filed on Mar. 19, 2012 and U.S. Provisional Patent Application No. 61/457,928 filed on Jul. 11, 2011.

The contents of the above applications are all incorporated by reference as if fully set forth herein in their entirety.

FIELD OF THE INVENTION

The present invention relates to the evagination and the grasping, fixating and fastening of a part in the human body (referred to hereinafter as "repositioning"). More particularly, the invention relates to a device that permits to perform a procedure that repositions the left atrial appendage of the heart.

BACKGROUND OF THE INVENTION

Atrial rhythm abnormalities are associated with the development of blood clots in the atrial chamber, which can result in the formation of thrombus and emboli which may (among other things) cause brain stroke. The left atrial appendage ("LAA") is particularly susceptible to clot formation. Several approaches were developed to reduce the risk of clot formation in the LAA, mainly consisting in physically separating or occluding the LAA from the left atrium. Said devices reduce the risk of blood clots in the LAA and/or obstruct or filter the flow of clots from the LAA into the atrium. One example of the separation devices are permanently-implanted occluders. Permanently-implanted occluders (e.g., Watchman®) are usually introduced transseptally up to the LAA by a delivery catheter and then the device is anchored at the desired location by fixation barbs or other methods.

Figure 1:
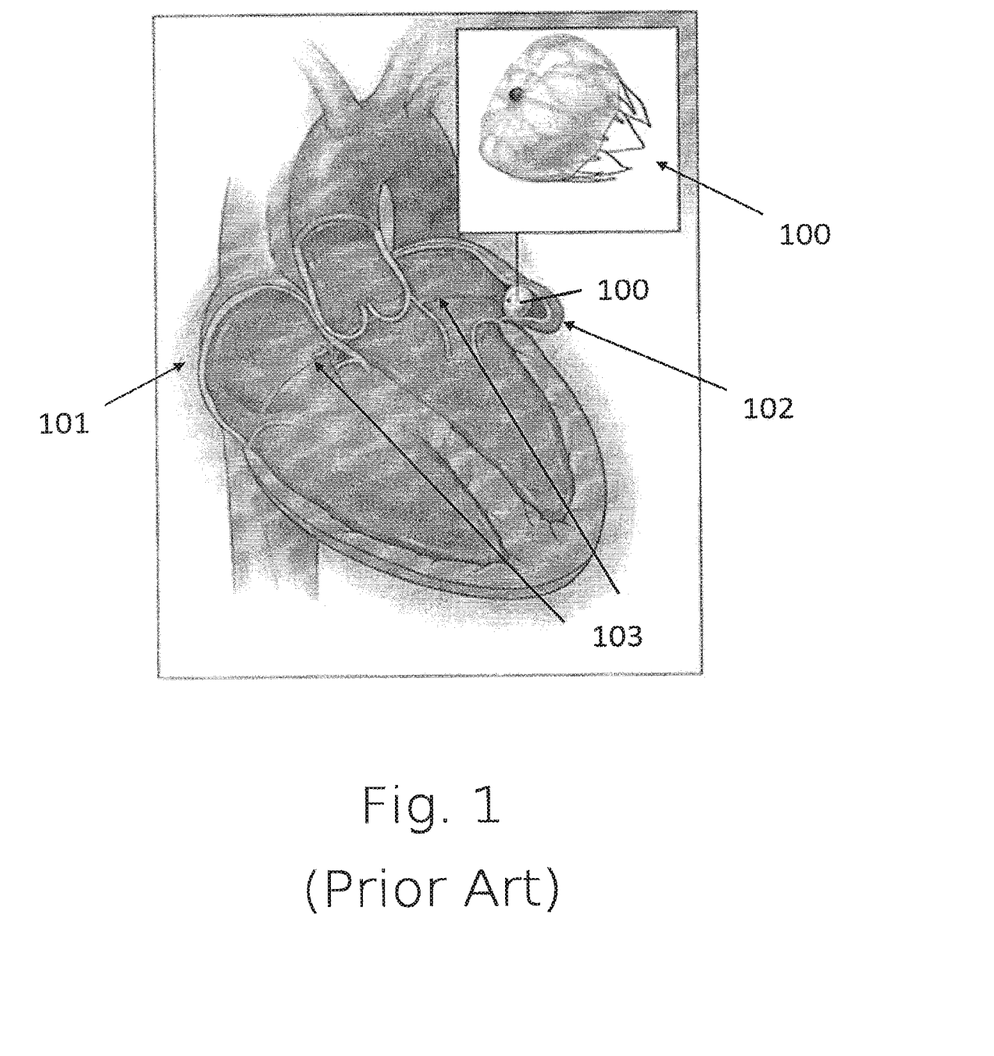
FIG. 1 illustrates the insertion of a prior art Watchman occlusion device into the LAA.

An example of such an occlusion device is shown in FIG. 1, which illustrates how a Watchman occlusion device 100 is introduced through the right atrium 101 and transseptally catheterized, as shown at 103, to reach the LLA 102 (image taken from http://www(dot)hkma(dot)org/english/cme/clinicalcase/201003a_set(dot)htm).

A second example of physical separation of LAA is described in U.S. Pat. No. 7,427,279, which discloses a closure catheter comprising deployable tissue anchors. The device is to be inserted up to the LAA. Once located properly, the anchors are deployed into the surrounding tissue and draw the tissue radially inwardly to close the LAA cavity.

A third example of physical separation of LAA are permanently implanted clip (e.g., The AtriClip™ LAA Exclusion System—http://www(dot)atricure(dot)com) which contains an LAA Clip for open occlusion of the heart's left atrial appendage. The Clip is pre-loaded on a disposable Clip applier. Said clips are located extraluminally, and require open-chest surgery.

Blood clot formation in the LAA is managed also by anticoagulant therapies, such as Warfarin (Coumadin). Said therapies cause significant complications in 1-2% of patients a year.

Although a variety of procedures has been suggested for overcoming the problem, all procedures known in the art are either long and complex, or present severe dangers resulting from perforation of the cardiac (left atrial and LAA) wall, or from the voluntary or involuntary removal of portions of the LAA, and many present both drawbacks. Therefore, so far the art has failed to provide a simple and safe method to perform the closure of the LAA, and no attempts have been made to evaginate it as a stage of a closure procedure.

It is an object of the invention to provide a method and apparatus for repositioning a body part.

It is another object of the invention to provide a device that permits to perform a medical procedure by which there is evagination and then constant fixation in the left atrium of the LAA, which can be safely performed without the danger of damaging the LAA tissue.

It is yet another object of the invention to provide a device suitable for carrying out a procedure at the end of which the repositioned LAA is covered by not-thrombogenic endocardium and cannot harbor blood clots.

Other objectives and advantages of the invention will become apparent as the description proceeds.

SUMMARY OF THE INVENTION

The invention in one aspect relates to a device for manipulating a body part, comprising:
  a) an elongated guide instrument provided with a tip suitable to be positioned in close juxtaposition with a tissue at a desired location of the said body part; and
  b) a suction channel terminating in or near said tip.

In one aspect, said manipulating comprises repositioning the body part.

According to one embodiment of the invention the suction channel terminates in a concave holder, such as, e.g., a holder selected from a cup, a cone, or other semi-spherical shape. The holder is preferably—but not limitatively—made of flexible material.

The device of the invention may further integrally comprise fastening means, or fastening means may be provided separately. In one embodiment of the invention the fastening means are actuatable from the elongated guide instrument. In another embodiment of the invention the fastening means comprise, at or near its proximal end, a string or the like flexible looped element. The flexible looped element may be conveniently provided in its pre-deployed position, such that it is looped around the axis of the elongated guide instrument.

In one embodiment of the invention the fastening means comprise a clipping or clamping fastener. In another embodiment of the invention the fastening means comprise a staple.

In a particularly interesting embodiment of the invention the device is suitable to reposition a body part, which is the left atrial appendage of a heart.

The suction channel can be also used for aspiring blood clots, especially those located in the LAA.

In another embodiment of the invention the device is suitable to secure and isolate polyps in the GI tract.

Also encompassed by the invention is a device, which is coupled to fastening means, which are not integral therewith. In one embodiment of such device, the fastening means comprise filling means suitable to fill the void created in the outer part of a heart, by the repositioning of the left atrial appendage of the heart. Suitable filling means comprise, e.g., a biocompatible glue.

The invention is also directed to a method for repositioning a body part, comprising positioning an elongated guide instrument provided with a tip in close juxtaposition with a tissue at a desired location, wherein said guide instrument is provided with a suction channel terminating in or near said tip and with fastening means actuatable from said elongated guide instrument.

BRIEF DESCRIPTION OF THE DRAWINGS

In the drawings.

All other figures schematically illustrates the operation of a device according to the invention, wherein.

DETAILED DESCRIPTION OF THE INVENTION

The present invention relates to a catheter-based device and method for the evagination and the grasping, fixating and fastening (collectively referred to herein as "repositioning") of a body part. In a particularly important application, said body part is the intraatrial left atrial appendage (LAA). Although the invention is in no way limited to use in the LAA, this procedure will be used in the description to follow, to illustrate the device of the invention and its use.

The procedures described herein can be carried out under vision, employing vision techniques such as fluoroscopy and transesophageal echo.

In a specific embodiment of the invention, the device comprises an elongated flexible guide instrument, a suction device and a device suitable to deploy a fastening accessory. Other devices regularly used in endoscopic surgery, such as light sources, cameras etc. can be also carried in the guide instrument, and such conventional apparatus is not described herein in detail, for the sake of brevity.

In a particular embodiment of the invention, the suction device and the device to apply a fastening accessory are located in the lumen of the guide instrument. Said fastening accessory can be of any suitable type and can be made of one piece or of a plurality of pieces. In one embodiment of the invention, the fastening accessory comprises one or more clips. In another embodiment the fastening accessory comprises one or more loops. Different fastening accessories can also be combined and various suitable accessories will be easily evident to the skilled person from the description to follow.

Transapex or transaortal or transatnial external through the pericard Transseptal access to the LLA is usually achieved by introducing a transseptal catheter through the femoral or jugular vein, and advancing the catheter transluminally into the right atrium. After locating the catheter in the right atrium, a long hollow needle is inserted transseptally by force through the fossa ovalis until attaining the left atrium, as seen at 100 in FIG. 1, with reference to the prior art method. Once in the left atrium, the catheter is advanced up to the LAA while monitored by any suitable method, such as echo- and/or fluoroscopic control. The device of the current invention is preferably inserted transseptally.

Figure 2:
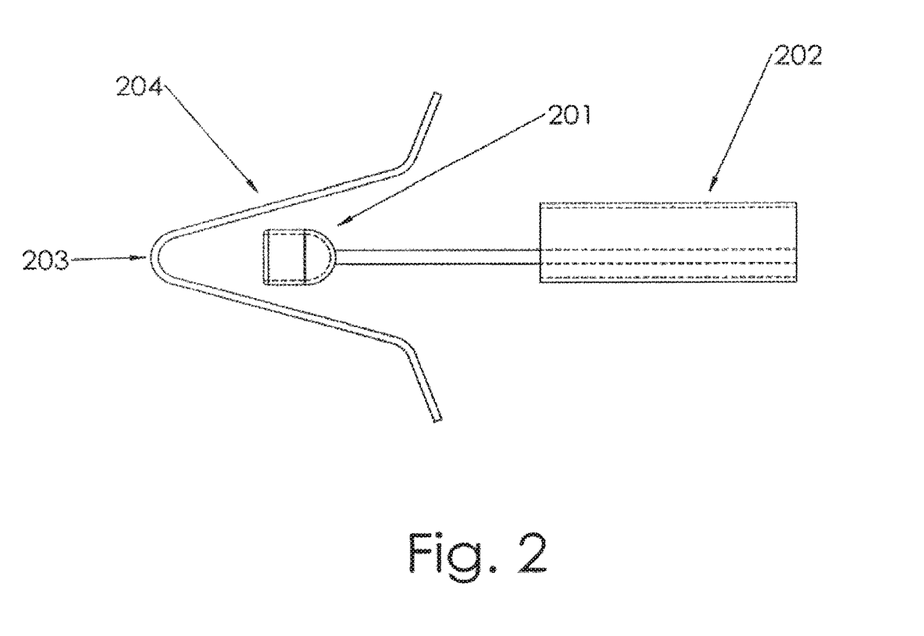
FIG. 2 illustrates the anatomical positioning of the guide instrument into the left atrium before entering the LAA and after inflating the suction catheter.
Figure 3:
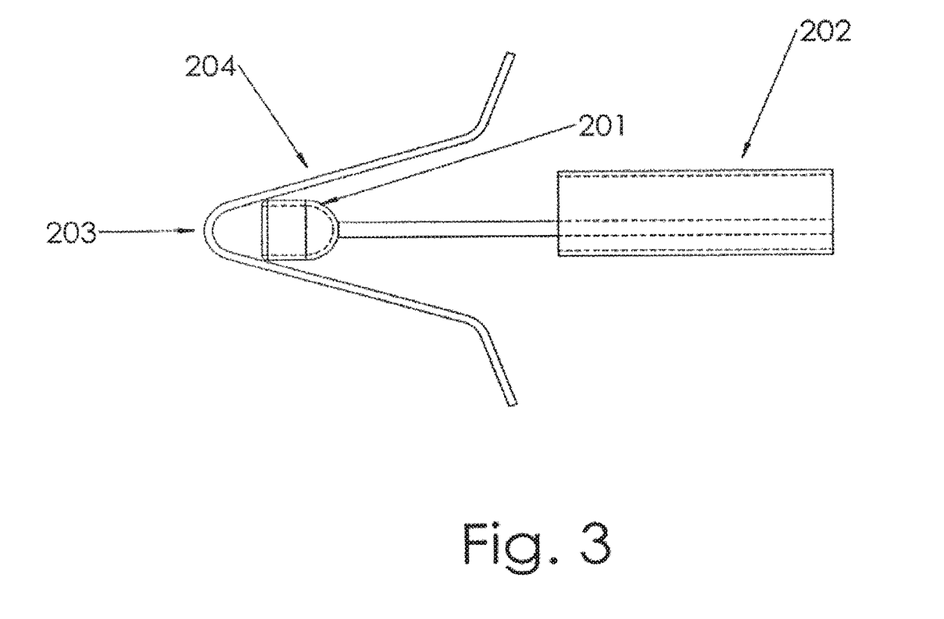
FIG. 3 illustrates the anatomical positioning of the guide instrument into the LAA before activating the suction device.
Figure 4A:
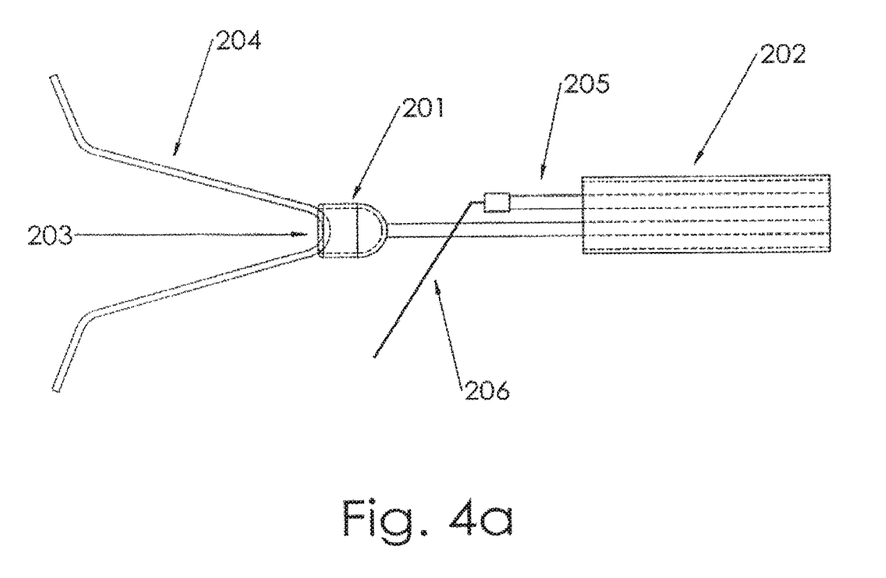
FIGS. 4*a* and 4*b* illustrate the reshaping of the LAA after pulling back the guide instrument.
Figure 4B:
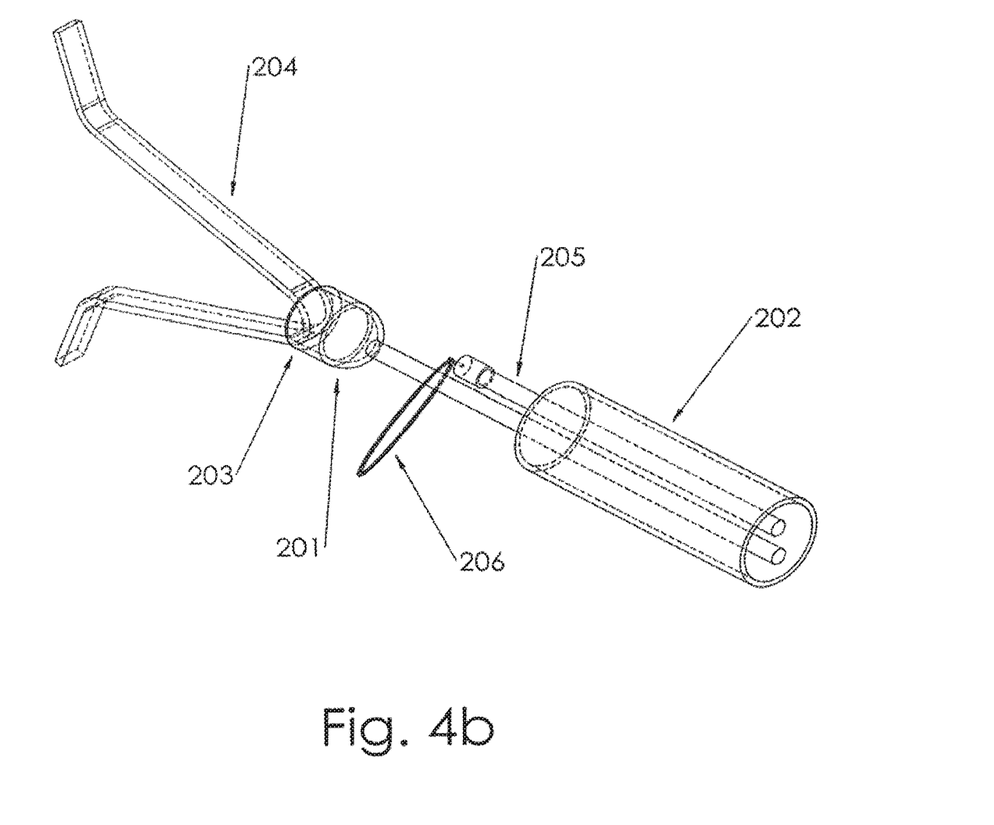
Figure 5A:
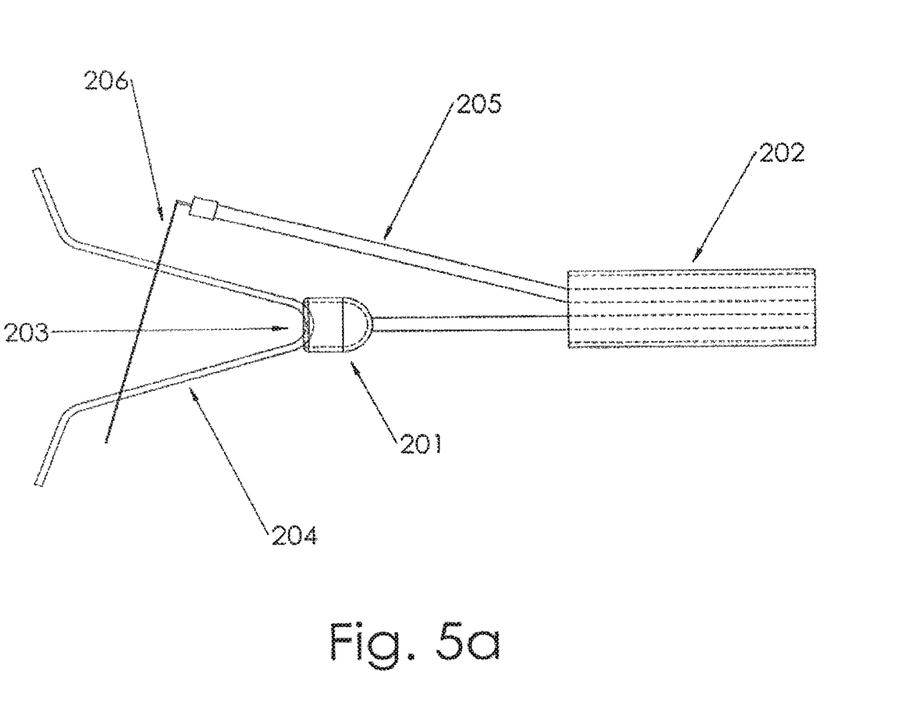
FIGS. 5*a* and 5*b* illustrate the application of an open clip to the base of the LAA.
Figure 5B:
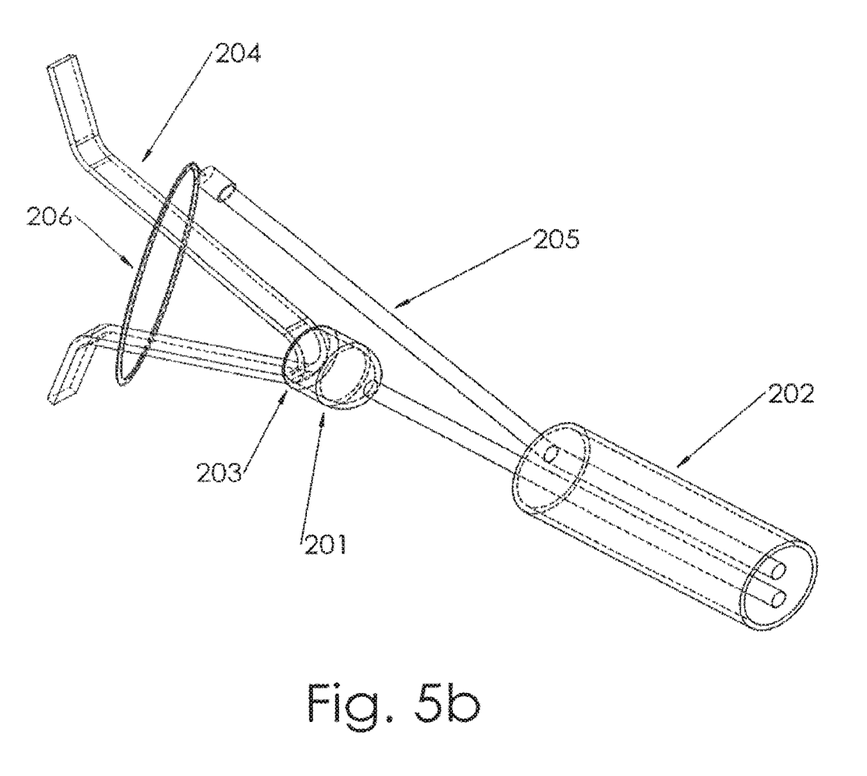
Figure 6A:
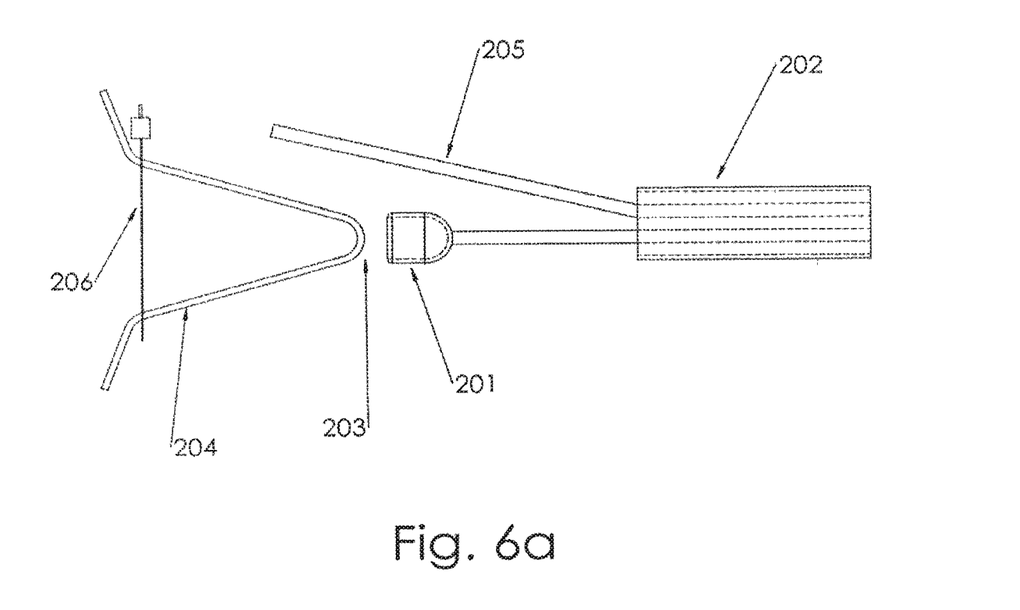
FIGS. 6*a* and 6*b* schematically illustrate the closed clip, lasso or suture.
Figure 6B:
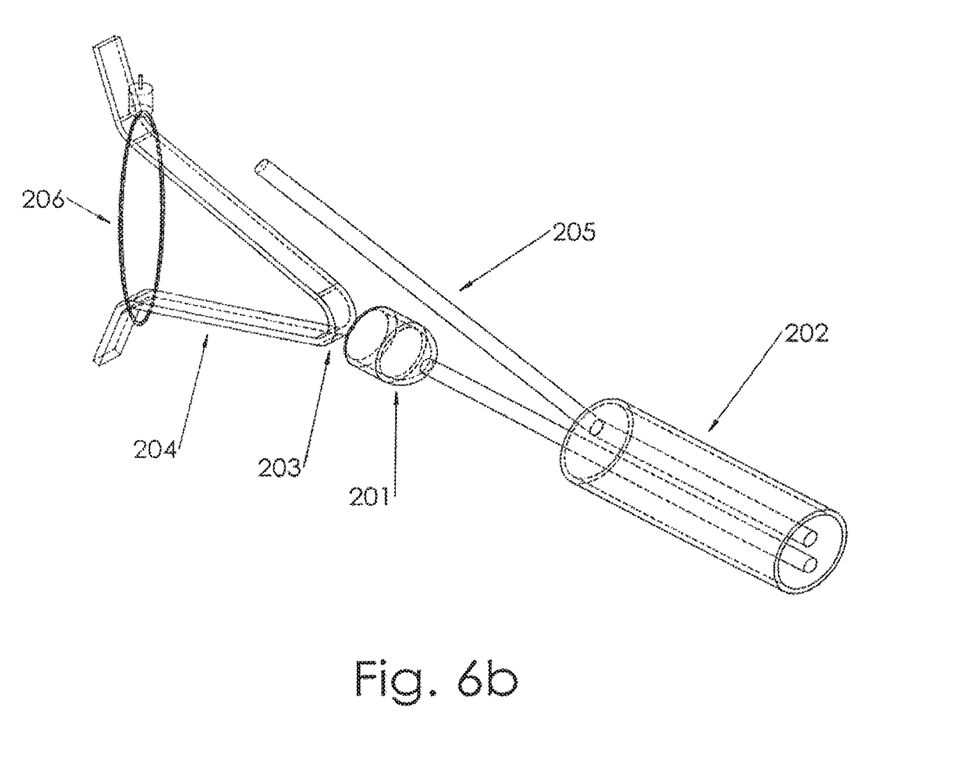

In one embodiment of the invention the catheter is provided at its tip with a suction channel that terminates in a concave holder selected from a cup, a cone or other semispherically shaped device, which is expanded after reaching the left atrium, thus preventing possible atrial and/or appendage wall perforation by the catheter tip. The suction channel can be also used for aspiring blood clots, especially those located in the LAA. Alternatively, a catheter tip can be made of any soft material that is less prone to cause perforation. As will be apparent to the skilled person, this safety feature (or an alternative one) is desirable but the invention can be carried out without it. The catheter is then inserted into the LAA (FIG. 2). Insertion of the catheter can again be guided by any suitable method, such as echo- and/or fluoroscopic control, direct or indirect vision, etc. Once the catheter is located in the LAA and touches the wall of the LAA, suction is applied through a channel connected with tip 201 (FIG. 3), such that tip 201 of catheter 202 holds portion 203 of the left atrial appendage 204 by suction. Thereafter, the catheter is pulled back into the left atrium under guided control, thus repositioning the left atrial appendage 204 into the left atrium (FIGS. 4*a* and 4*b*). The repositioned appendage at this time is held by suction. A fastening accessory is applied to the intraluminar base (FIGS. 5*a* and 5*b*) of the repositioned left atrial appendage, to permanently prevent its return into the normal position. The fastening accessory can be a clip, suture or loop 206, or an accessory combining a clip and a loop, or any other suitable fastening means. In the example of the loop suitable arrangements are provided, e.g., a screw assembly, to detach it from its guide 205 after fastening is completed. After applying the fastening accessory, suction can be discontinued and the catheter removed (FIGS. 6*a* and 6*b*).

At the end of the procedure the LAA is repositioned into the left atrium and held by a fastening accessory. When operating according to the embodiment described above, as well as with other embodiments of the invention, no pins, hooks or other sharp and penetrating parts on the atrial wall are used, and no penetration of atrial wall outside to pericardium is performed.

When operating according to the invention, suction, of up to 1 atmosphere can be employed without substantial fear of damage to the tissue. The force applied to fixate the appendage base with a lasso or clip must be calculated so as not to impart damage. For instance, said force can be up to 3 kg, preferably 2 kg, provided the wire of lasso is at least 0.7 mm nitinol in diameter and the clip bar of the similar size at least are safe.

Figure 7A:
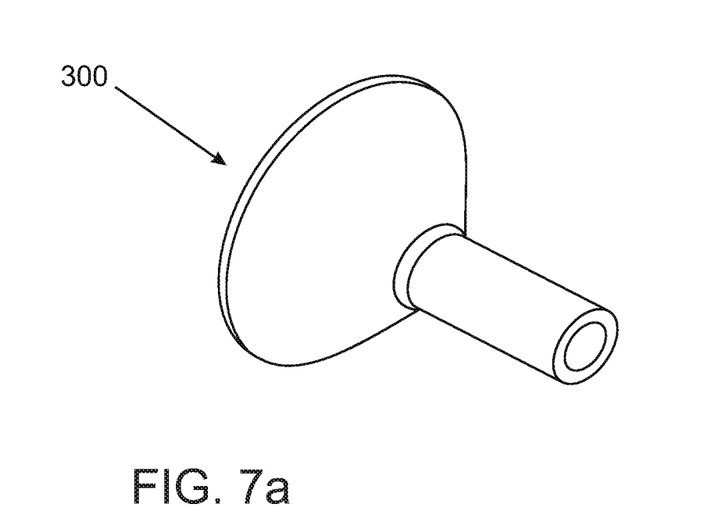
FIGS. 7*a* and 7*b* show a device according to one embodiment of the invention.
Figure 7B:
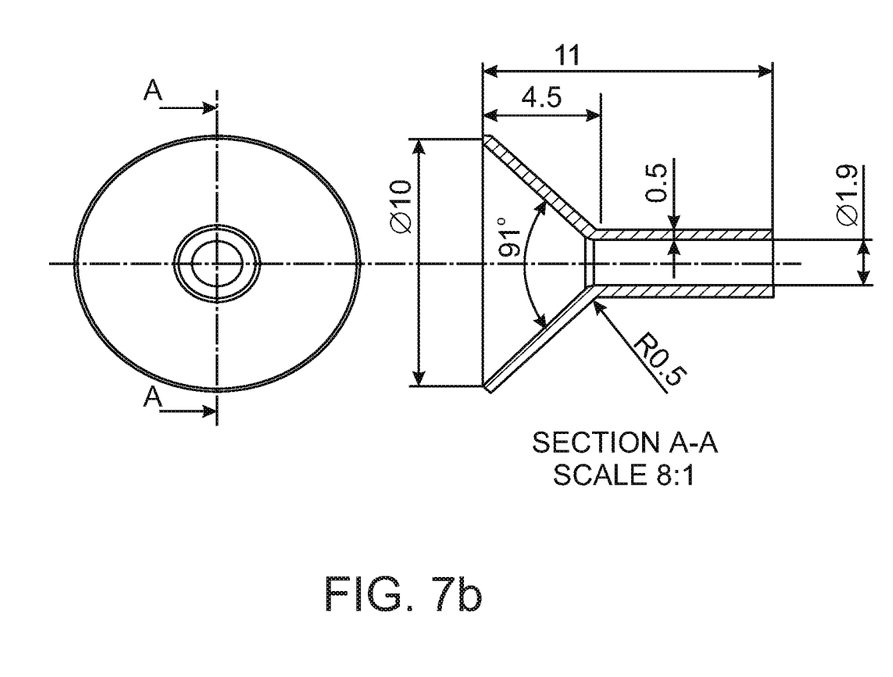

FIG. 7*a* and FIG. 7*b* illustrates the actual size of the suction device employed in in vivo experiments carried out with a pig heart. Pig hearts carry substantial similarity to human hearts in respect of the LAA problem and, therefore, were selected form the experiment.

Experimental Procedure and Selection of Operating Conditions

The above-illustrated procedure was carried out, in vivo, using a nitinol wire of 0.7 mm diameter as a lasso that created the loop 206 of the figures. As said, forces of 2-3 Kg were applied without any damage to the LAA tissue. However, should a practitioner wish to employ different operating conditions than the above, the following procedure should be followed:

1. Selection of Standard Substrate

A standard substrate, such as a silicone cylinder of 1 cm diameter is selected. Any other suitable soft material can be employed.

2. Determination of Standard Penetration Depth

The standard penetration depth with the selected material is determined by wrapping a lasso made of 0.7 mm diameter nitinol wire and applying a force of 2 Kg on the wire. When application of the force is completed the wire is removed and the depth to which it has penetrated the selected standard substrate is measured.

3. Determination of Alternative Operating Conditions

To determine a suitable set of operating conditions with a different type of wire, the selected wire is wrapped around the selected standard substrate as in 2 above, and forces of different magnitude are applied. The depth of penetration with each force applied is then measured. The force to be used with the newly selected wire is that which created a penetration depth essentially of the same magnitude as obtained in (2) above.

In an alternative embodiment of the invention fastening means are used, which are not integral with the guide introduced into the heart. In such a device the fastening means comprise filling means suitable to fill the void created in the outer part of a heart, by the repositioning of the left atrial appendage of the heart. Such filling means comprise, e.g., a biocompatible glue.

An alternative fixation method involves fixating the evaginated appendage in its position achieved after suction and traction, by anchoring it to the cardiac wall, for example to the interatrial septum.

In an alternative embodiment of the invention the device of the invention can be used in endoscopy of gastrointestinal, urinary, airway or any other tract to grasp (with suction) and to put a loop (clip) on polyps, tumors etc. Such uses also form a part of the invention.

The skilled person will devise many other additional uses of the device of the invention. For instance, suction can be applied through the suction channel to remove blood clots from the LAA, prior to any other operations.

As will be apparent to the skilled person from the above description, the invention affords the means for performing an effective and safe procedure, which was not available in the art before the invention. Although the invention has been described using a preferred embodiment by way of illustration, the skilled person will easily appreciate the many alternative ways in which the invention can be carried out.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A device for manipulating a left atrial appendage (LAA) of a heart, comprising: an elongated and hollow guide instrument which is shaped and sized to be transvascularly and transseptally introducible into a left atrium (LA); a suction channel passing through said guide instrument, said suction channel terminating with a flexible soft holder, wherein said suction channel and said flexible soft holder are shaped and sized to be enclosed within a lumen of said guide instrument during said transvascular and transseptal introduction into said LA and to forwardly extend from said lumen of said guide instrument after reaching the LA, and wherein said flexible soft holder is configured to expand; a suture loop fastener shaped and sized to be enclosed within said lumen of said guide instrument during said transvascular and transseptal introduction into said LA and to forwardly extend from said lumen of said guide instrument, wherein said flexible soft holder is configured to radially expand, wherein said flexible soft holder is configured to be positioned in close juxtaposition with a cavity of the LAA, and to hold and to draw a portion of the LAA into said flexible soft holder upon application of suction through said suction channel so that said held and drawn LAA portion is repositionable to be inverted into the LA by retraction of said flexible soft holder; and wherein said suture loop fastener is configured to be positioned around said repositioned LAA portion, to permanently prevent return of said repositioned LAA portion into said LAA.

2. A device according to claim 1, wherein said flexible soft holder is configured to facilitate application of suction without imparting damage to the repositionable LAA portion.

3. A device according to claim 1, wherein said suture loop fastener comprises a wire shaped as a loop.

4. A device according to claim 1, wherein said flexible soft holder is selected from a cup, a cone, or other semi-spherical shape.

5. A device according to claim 1, wherein said flexible soft holder is made of flexible material.

6. A device according to claim 1, wherein the suture loop fastener is configured to avoid perforation of the LAA when actuated.

7. A device according to claim 1, wherein the suture loop fastener is actuatable from the elongated guide instrument.

8. A device according to claim 7, wherein the suture loop fastener comprises:
   a) a guide disposed internally within the elongated guide instrument;
   b) a wire shaped to form a loop, received within, and attached to, said guide;
   c) an actuator configured to discharge said loop-shaped wire from a distal end of said guide and to cause said discharged loop-shaped wire to completely encircle an intraluminar base of the repositioned LAA portion until fastening is completed, to permanently prevent return of the repositioned LAA portion to its normal position; and
   d) a detachment facilitating element configured to detach said looped-shaped wire from said guide after fastening is completed.

9. A device according to claim 8, wherein the loop-shaped wire is looped around an axis of the elongated guide instrument.

10. A device according to claim 1, which is suitable such that the repositioned LAA portion is coverable by non-thrombogenic endocardium.

11. A device according to claim 1, wherein when expanded, a tip of said flexible soft holder is wider.

* * * * *